US011857452B2

(12) United States Patent
Nuzer

(10) Patent No.: US 11,857,452 B2
(45) Date of Patent: *Jan. 2, 2024

(54) METHOD AND APPARATUS FOR RESTRAINT ANCHOR

(71) Applicant: Andrew Nuzer, Point Pleasant, NJ (US)

(72) Inventor: Andrew Nuzer, Point Pleasant, NJ (US)

(73) Assignee: Indnrn Holdings, LLC, New (JE)

( * ) Notice: Subject to any disclaimer, the term of this patent is extended or adjusted under 35 U.S.C. 154(b) by 0 days.

This patent is subject to a terminal disclaimer.

(21) Appl. No.: 17/498,691

(22) Filed: Oct. 11, 2021

(65) Prior Publication Data

US 2022/0023089 A1 Jan. 27, 2022

Related U.S. Application Data

(63) Continuation of application No. 16/849,925, filed on Apr. 15, 2020, now Pat. No. 11,141,305.

(51) Int. Cl.
*A61F 5/37* (2006.01)
*A44B 11/25* (2006.01)
*A47B 91/08* (2006.01)

(52) U.S. Cl.
CPC ........ *A61F 5/3776* (2013.01); *A44B 11/2588* (2013.01); *A47B 91/08* (2013.01)

(58) Field of Classification Search
CPC .. A61F 5/3776; A61F 5/3769; A44B 11/2588; A47B 91/08
See application file for complete search history.

(56) References Cited

U.S. PATENT DOCUMENTS 6,209,544 B1 * 4/2001 Ek .................. A61F 5/3776
                                                  128/869
6,955,511 B1 * 10/2005 Preta ............... B60P 7/0807
                                                  410/106

(Continued)

FOREIGN PATENT DOCUMENTS

| CA | 3057904 A1 * 12/2018 | ............. E05B 1/003 |
|---|---|---|
| GB | 2502290 A * 11/2013 | ............... A47H 1/10 |
| WO | WO-2009132390 A1 * 11/2009 | ............... A62B 1/04 |

OTHER PUBLICATIONS

Powers 09510 dual expansion bolt anchor sold on amazon.com dated Mar. 4, 2014, weblink: https://www.amazon.com/Powers-Fastening-Innovations-09510-Expansion/dp/B00ITGBBLE (Year: 2014).*

*Primary Examiner* — Terrell L McKinnon
*Assistant Examiner* — Ding Y Tan
(74) *Attorney, Agent, or Firm* — Brian K. Johnson, Esq., LLC

(57) ABSTRACT

An anti-ligature restraint device is provided. The device includes a tub secured to a mounting location. A sealing element is inserted into the tub. The sealing element includes a restraint element slot to which a restraint is secured when the device is in an open position. The sealing element is disposed entirely with the tub in the closed position. A spring within the tub provides resistance to the sealing element as it is pushed into the tub and rotated to secure the sealing element within the tub. A lid lock secures the sealing element in the closed position. The device may be used in the concrete floor of a hospital room. In the open position, the device secures patient restraints. In the closed position, the device is flush with its mounting surface and locked, thereby preventing patient tampering or access to harmful elements thereof.

11 Claims, 16 Drawing Sheets

(56) References Cited

U.S. PATENT DOCUMENTS

| | | | | |
|---|---|---|---|---|
| 7,654,027 | B1* | 2/2010 | Grover | F16B 21/165 |
| | | | | 403/322.2 |
| 10,610,037 | B1* | 4/2020 | deLoache, III | A47G 25/0642 |
| 10,837,191 | B1* | 11/2020 | Erbes | E04H 4/1663 |
| 11,038,331 | B1* | 6/2021 | Baldwin | H01R 13/447 |
| 2018/0347229 | A1* | 12/2018 | Riley | E05B 3/06 |
| 2019/0254898 | A1* | 8/2019 | Karl | A61G 7/05 |
| 2020/0206014 | A1* | 7/2020 | Richardson | A47B 97/00 |
| 2020/0289305 | A1* | 9/2020 | Wendt | A61F 5/3776 |
| 2021/0127832 | A1* | 5/2021 | Shahzad | A47B 97/00 |

* cited by examiner

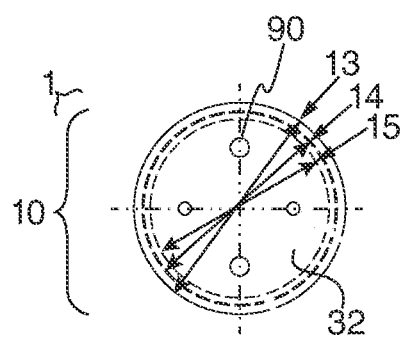
FIG. 1A
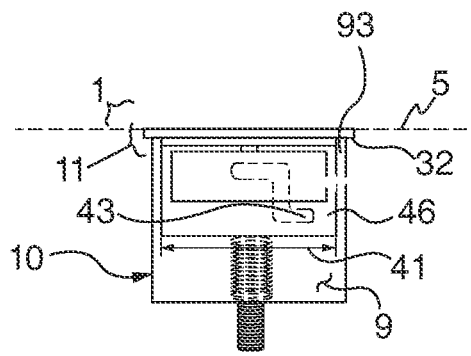
FIG. 1B
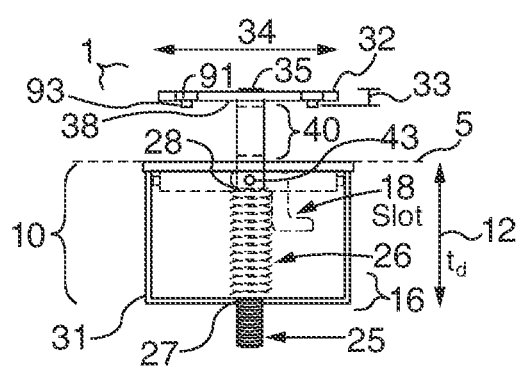
FIG. 1C
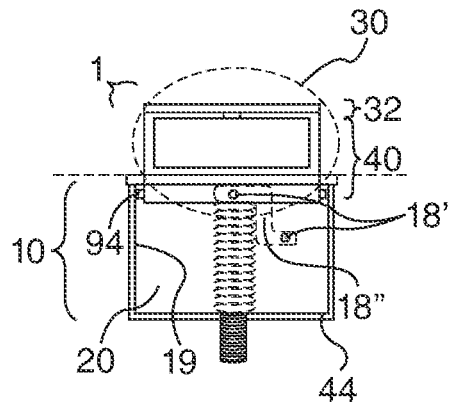
FIG. 1D
FIG. 1

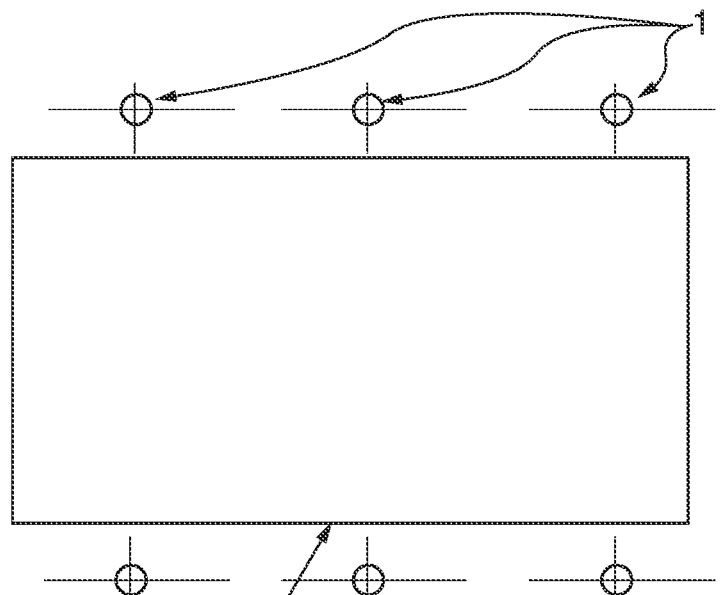
FIG. 2A
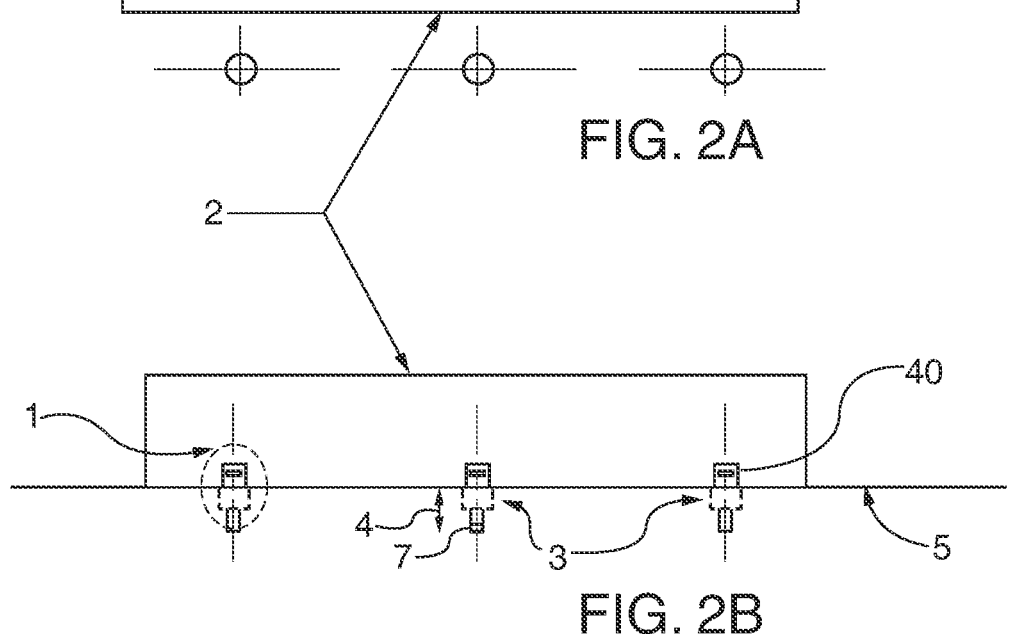
FIG. 2B
FIG. 2

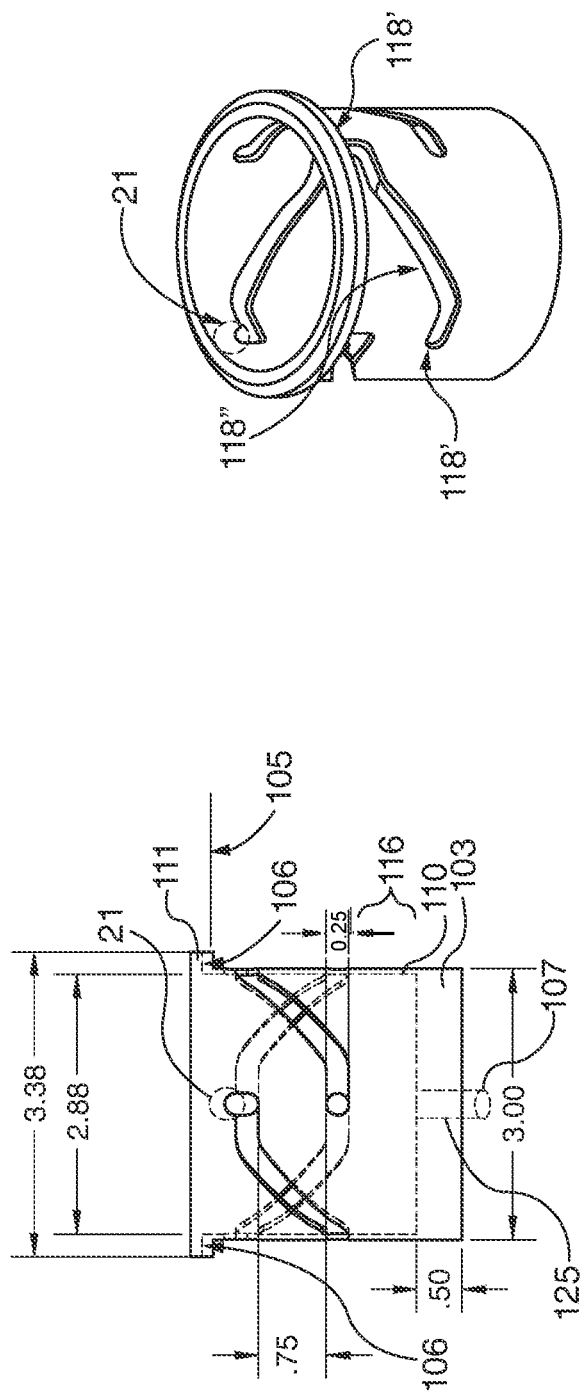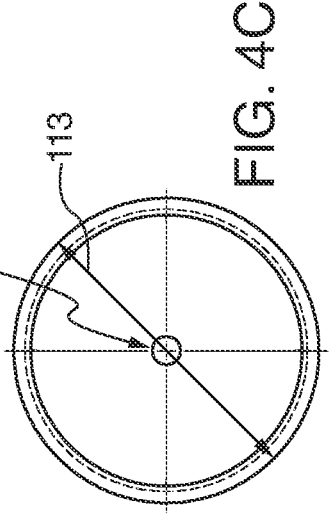

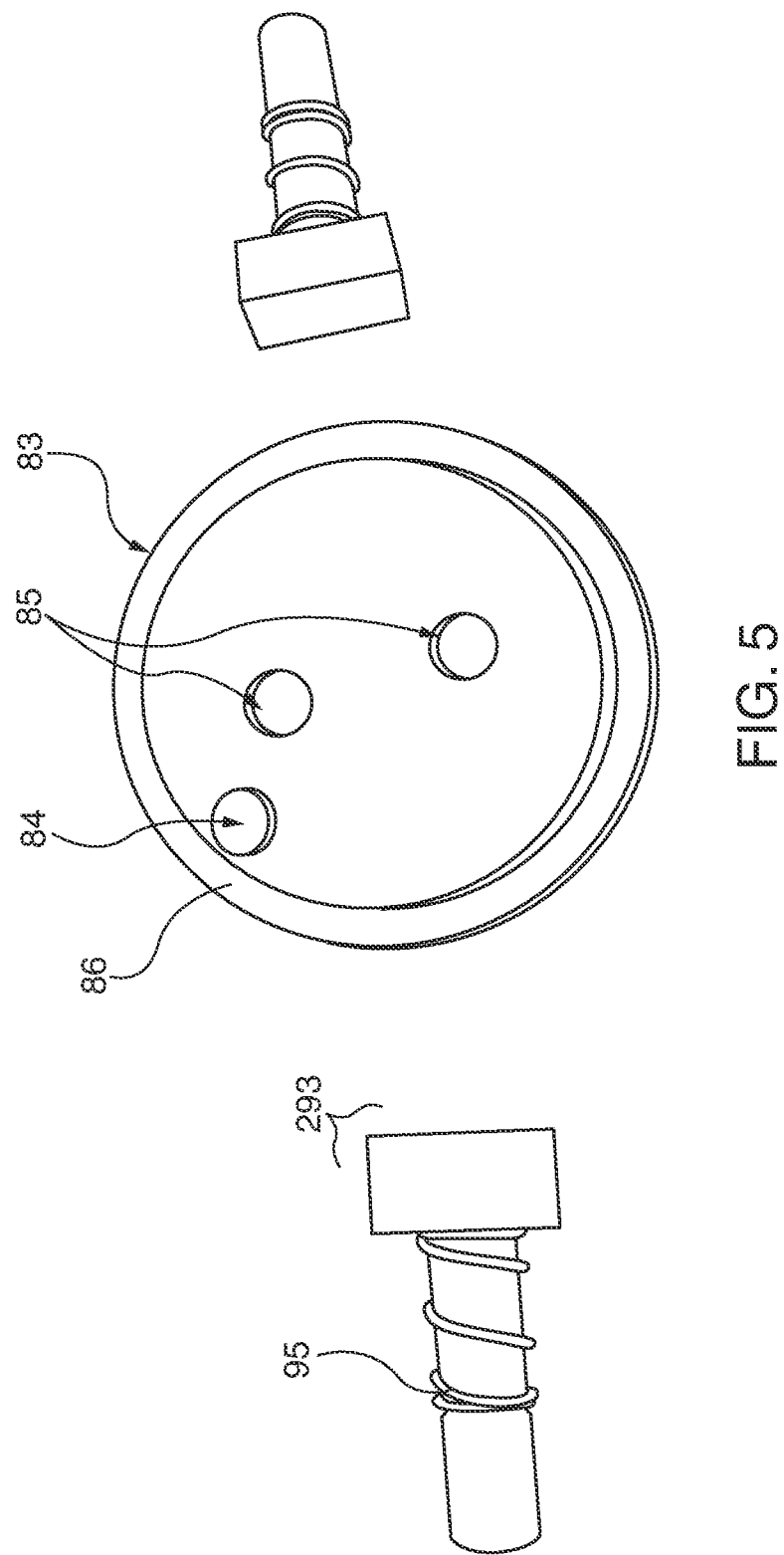

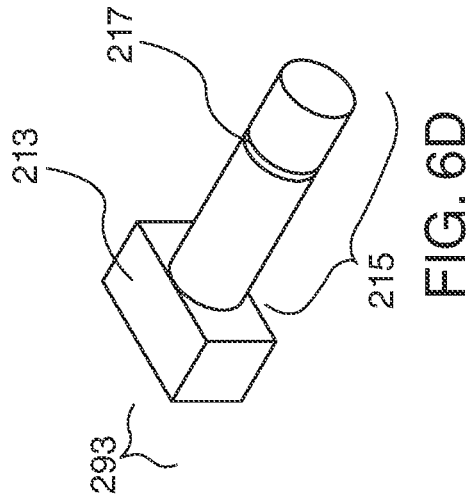
FIG. 6B
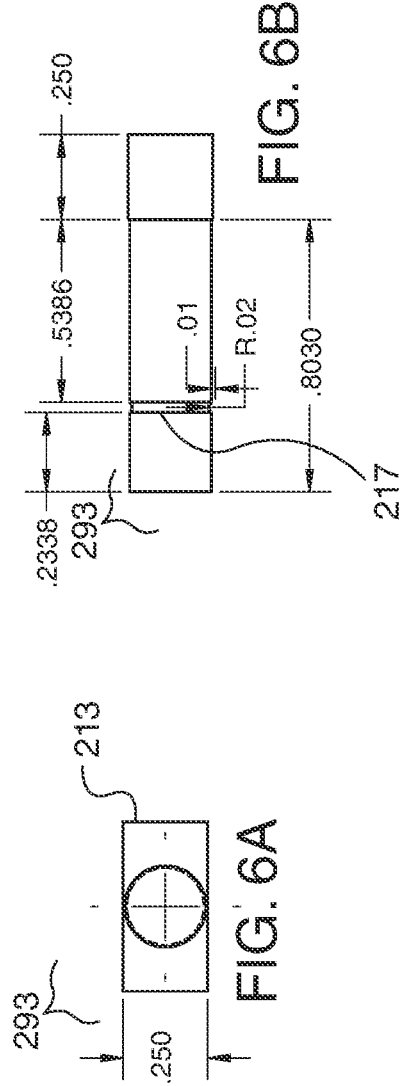
FIG. 6A
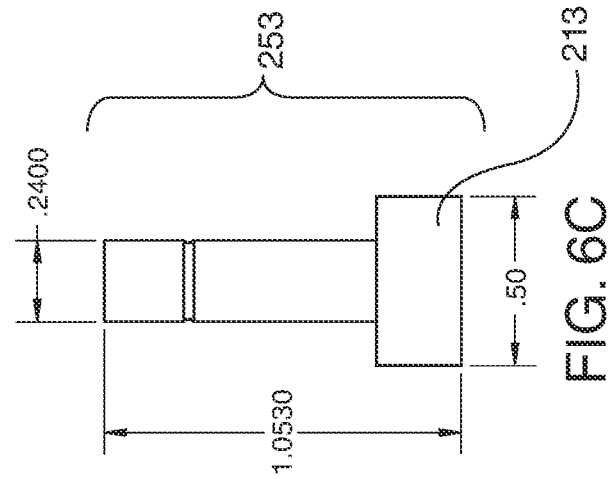
FIG. 6D
FIG. 6C
FIG. 6

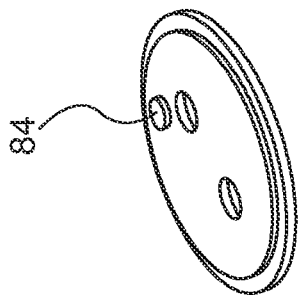
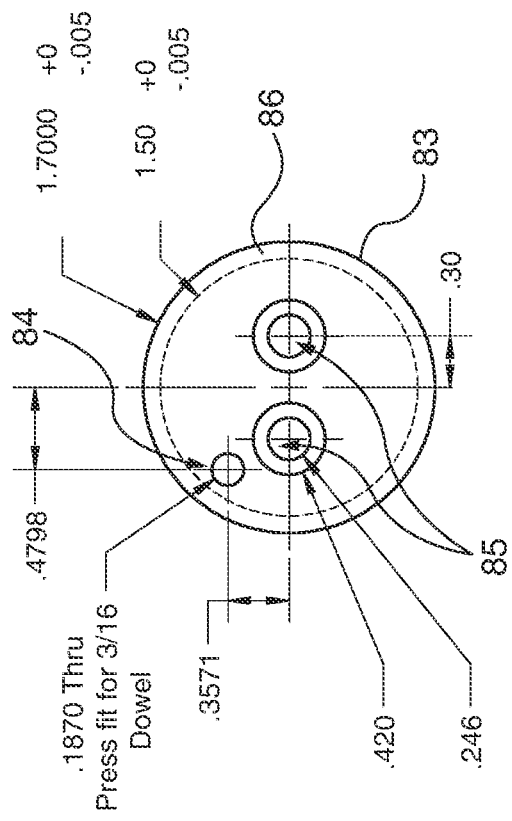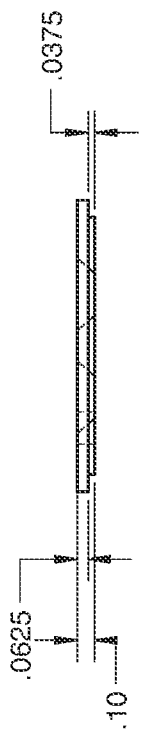
FIG. 7

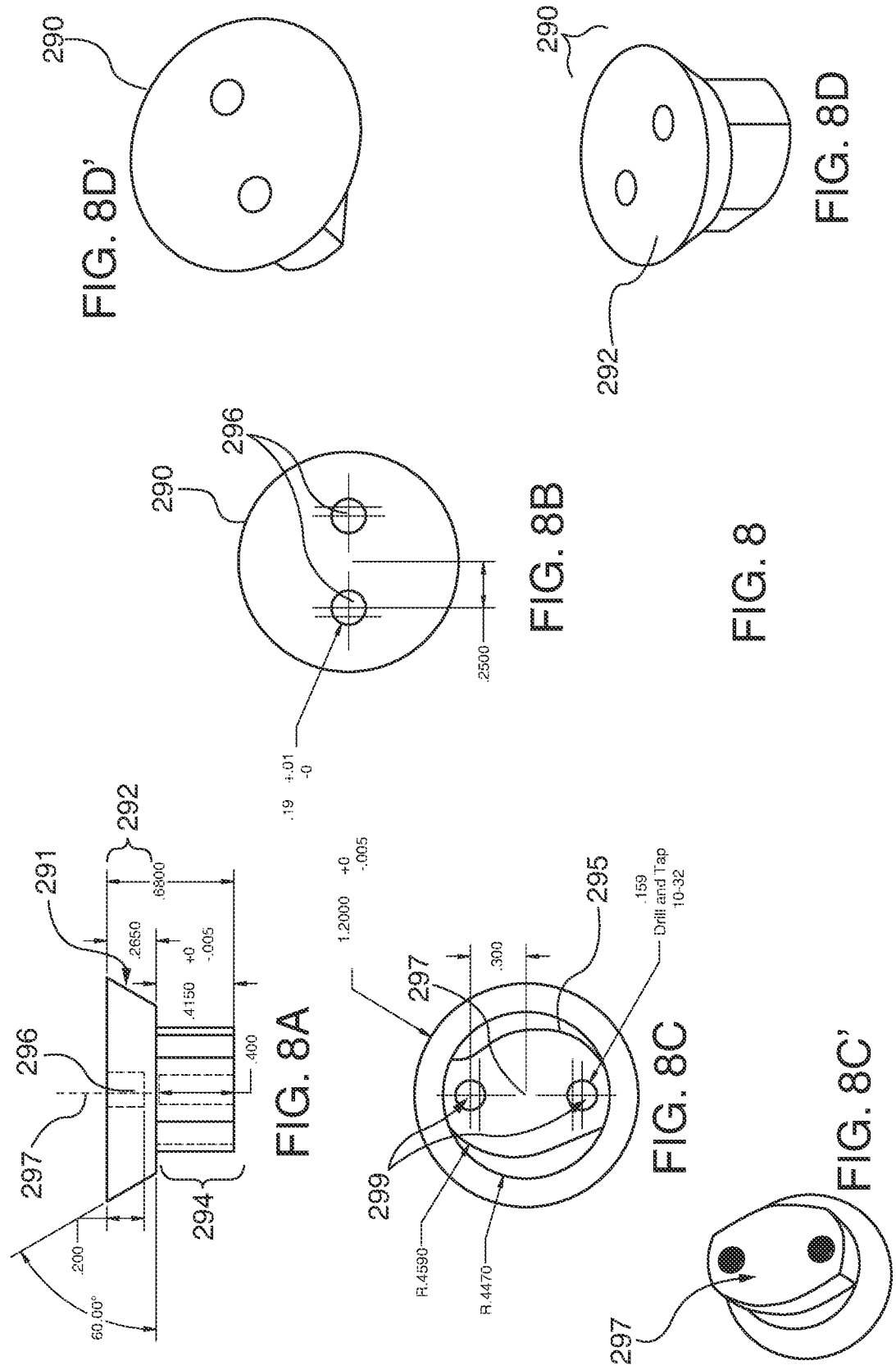

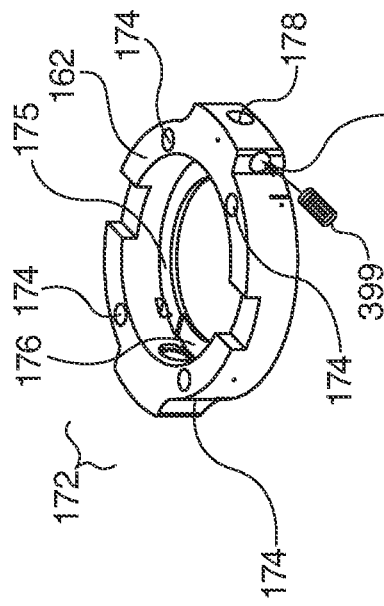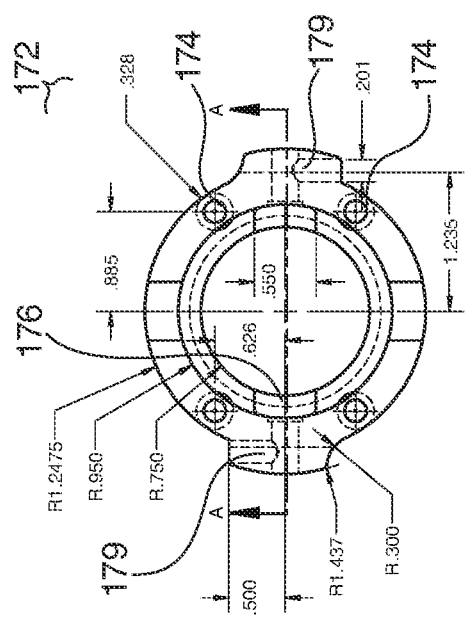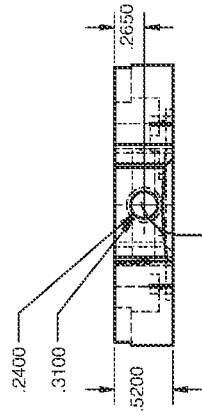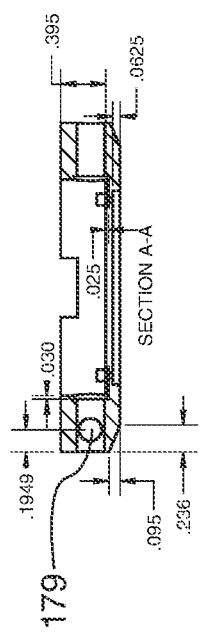
FIG. 9A  FIG. 9B  FIG. 9C  FIG. 9D
FIG. 9

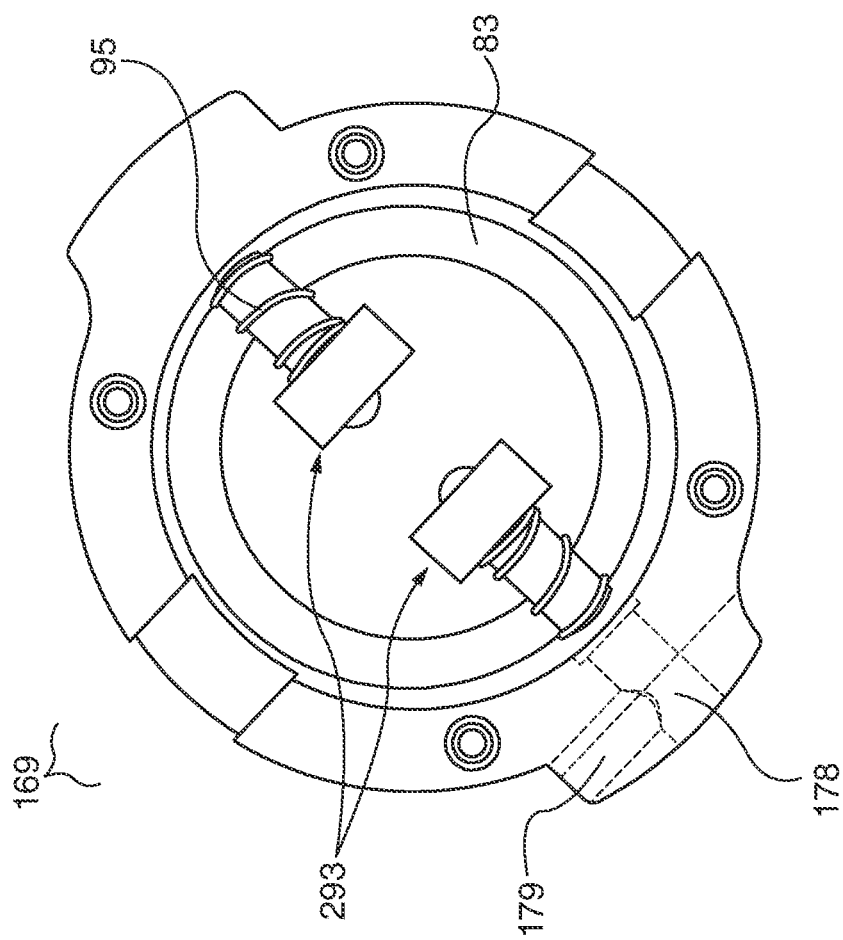

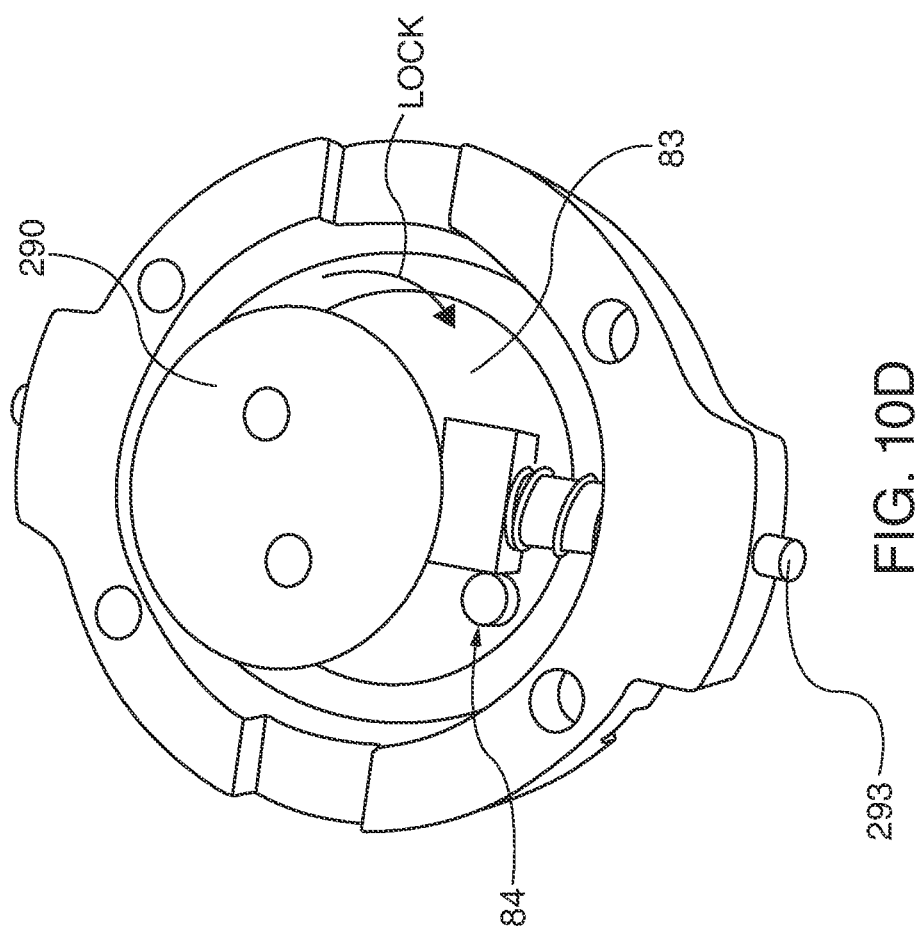

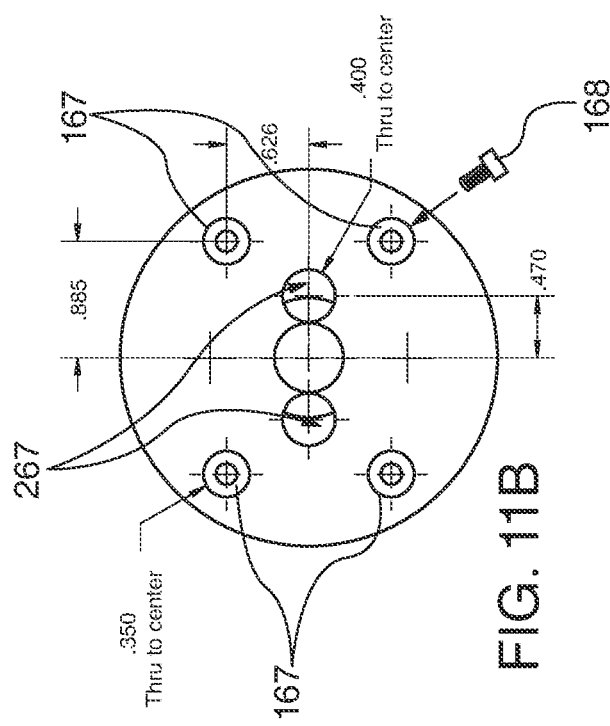
FIG. 11B
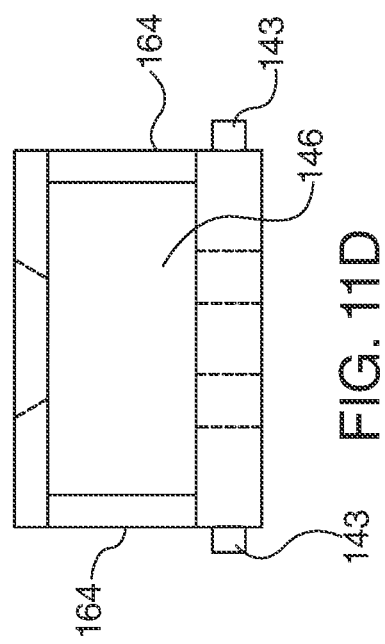
FIG. 11D
FIG. 11
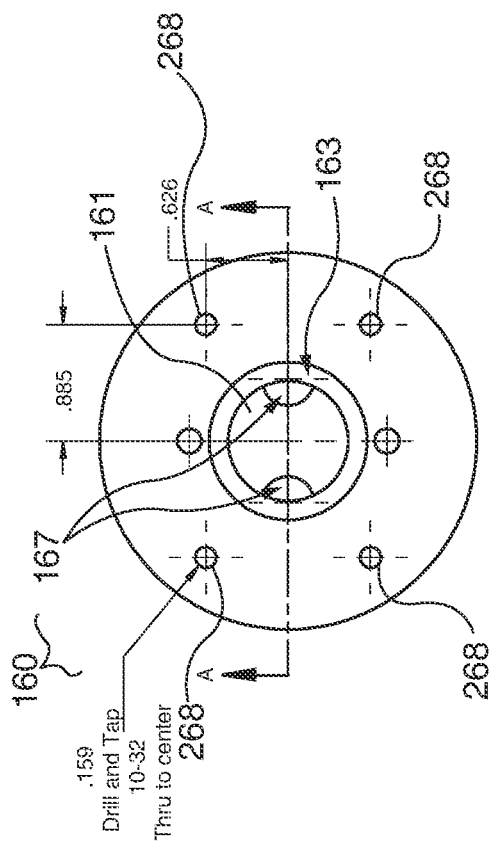
FIG. 11A
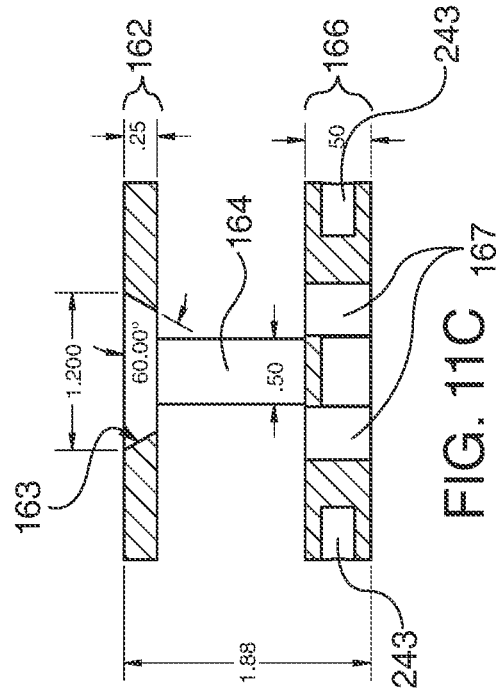
FIG. 11C ated Oct. 12, 2021, which in turn is a non-
METHOD AND APPARATUS FOR RESTRAINT ANCHOR

CROSS-REFERENCE TO RELATED APPLICATIONS

This application is a continuation of non-provisional utility U.S. patent application Ser. No. 16/849,925, titled METHOD AND APPARATUS FOR RESTRAINT ANCHOR" filed on Apr. 15, 2020, now U.S. Pat. No. 11,141,305 issued Oct. 12, 2021, which in turn is a non-provisional utility U.S. Patent Application that claims priority to two U.S. Provisional Patent Application Ser. No. 62/834,355, titled "METHOD AND APPRARTUS FOR RESTRAINT ANCHOR" filed on Apr. 15, 2019 and Ser. No. 62/874,615, titled "METHOD AND APPRARTUS FOR RESTRAINT ANCHOR" filed on Jul. 16, 2019. The entire contents of each and every one of these patent applications is incorporated by reference as if set forth herein in their entirety into the present patent application as if written into the same.

COPYRIGHT & TRADEMARK/TRADENAME NOTICES

A portion of the disclosure of this patent document may contain material, which is subject to copyright protection. The owner has no objection to the facsimile reproduction by any one of the patent document or the patent disclosure, as it appears in the Patent and Trademark Office patent file or records, but otherwise reserves all copyrights whatsoever.

BACKGROUND OF THE INVENTION

1. Field of the Invention

The invention relates to the provision of an anti-ligature restraint anchor. In particular, secure hospital settings such as those for the mentally and emotionally challenged, require certain secure restraint mechanisms. In a first, operable, position the restraint mechanism provides a patient restraint securing location at which point a secure strap or other restraint may be secured. In a second, safe and secure, position the restraint mechanism is "closed" or "inaccessible" such that the hospital patient has no useful access to the mechanism. In this second position, the patient cannot use the device to cause harm to themselves. Such a device provides proper and secure restraint in the first position when the patient requires restraint, while providing a safe, anti-ligature enclosure in the second position when the patient is free to move about and has potential access to the restraint device.

As evident to those skilled in the art, the use of the devices disclosed in the present invention may also be used in other environments to provide similar functions. For example, any location requiring secure holding locations are candidates for the use of the present invention including but not limited to jail cells, prisons, airports, pet or livestock staging locations etc.

2. Description of Related Art

Prior art devices are available in the anti-ligature space and include institutional apparatus for all aspects of protected environments. Various shower installations, shower heads, door handles, beds, door frames and other similar apparatus are available for safe use within such protected environments. However, no devices are available that provide an intentional ligature point such that the intentional ligature is capable of being conveniently and safely hidden without removing it from the protected environment when not in use.

US Pat. Pub. No. 2011/0198458A1 (Karl, et al.) discloses a temper resistant guide for furniture. The tamper resistant glide assembly comprises a foot, a stem and an insert connected to a leg of the furniture. The foot has a having a top and a bottom; and the bottom is adapted to engage a floor surface. A stem mount on the top of the foot provides an adjustable attachment to a first end of the stem. The stem has a second end spaced from the top of the foot and a threaded portion in between the first end and the second end. An insert captured on the stem. The insert is threadably engaged to the stem by a generally cylindrical body with a threaded passage extending through the body adapted to matingly engage the threaded portion of the stem. A cap fixed on the second end of the stem to capture the insert. The insert disposed in a generally vertical passageway formed in the furniture and fixed therein to secure the glide assembly to the leg. The insert recessed into the leg to prevent prying or forcible removal without destruction of the furniture. While the tamper resistant guide securely hold down a piece of furniture, it does not have any hidden ligature functionality.

Norix Group Inc. makes a product line of ligature resistant beds. The beds are advertised as being used by behavioral healthcare professionals where traditional furniture is completely unsuitable for critical environments. The Norix bed is designed to provide the strength, safety and cleanability required for the daily rigors of institutional living, molded in specially formulated, high-impact, fire-retardant polyethylene, structurally enhanced for increased strength and durability. These beds feature seamless construction with rounded corners for added safety and security. The beds are designed to be attached flush to the wall or floor. However, the anti-ligature nature of the bed is more in the nature of having no ligature points at all on the furniture. Nothing in the Norix product line provides for a restraint point on the furniture or elsewhere such that it can be conveniently hidden and made inaccessible when not in use.

Thus, a need exists in the art for an improved restraint anchor that provides an improved restraint securing mechanism which is safe for use in a clinical environment and in which anti-ligature aspects are required when not in use.

BRIEF SUMMARY OF THE INVENTION

Accordingly, in one particularly preferred embodiment, An anti-ligature device for use with restraints, is provided, the restraints used within an environment, the environment has a mounting location, the mounting location including a hole into which the anti-ligature device is mounted, the anti-ligature device including: a tub, the tub being open at one end, the tub has an outer surface and an inner surface, the tub inner surface partially defining an inner cavity, the tub being dimensioned for insertion into the mounting hole such that the tub fits within the hole, the tub outer surface being inaccessible from the environment when the tub is inserted into the hole; a tub securing element, the tub securing element secured to the inner surface of the tub and the mounting location; a compressible element has a first end and a second end, the compressible element disposed within the inner cavity of the tub and coupled at the first end to the tub; a tub sealing element, the tub sealing element has a restraint element for engaging the restraints, the tub sealing element coupled to the compressible element at the second end, the tub sealing element has an insertion portion and a top sealing portion, the top sealing portion of the tub sealing element coupled to the insertion portion, the insertion portion compressing the compressible element when the tub sealing element is inserted into the tub such that the tub sealing element is under force by action of the compressible element when inserted into the tub; at least a portion of the tub sealing element being exposed to the environment in an open position of the anti-ligature device, the restraint element for engaging the restraints being accessible in the open position, and the tub sealing element being inserted into the tub in a closed position of the anti-ligature device, the restraint element being disposed entirely with the tub in the closed position, and the tub sealing portion of the tub sealing element sealing the open end of the tub in the closed position.

In other particular preferred variations of the device, the device further provides the environment is a room and the restraint is a restraining strap for restraining a person, the restraint element is a slot for receiving the restraining strap, and the mounting location within the environment is one of a floor, a wall, or a piece of furniture; or the tub has a top surface at the open end, the top sealing portion of the tub sealing element has a top surface, the top surface of the tub and the top surface of the tub sealing element meeting to provide the seal between the tub sealing element sealing and the open end of the tub in the closed position; or the tub has a top surface at the open end, the open end of the tub has a circumference profile, the top sealing portion of the tub sealing element has a top surface, the top surface of the top sealing portion has a circumference profile, the circumference profiles of the open end of the tub and the tub sealing element being identical in shape, the circumference profile of the open end of the tub being slightly larger than the circumference profile of the tub sealing element, the top sealing portion of the tub sealing element fitting within the open end of the tub in the closed position such that the top surface of the tub is substantially coplanar with the top surface of the tub sealing element, the seal being provided by a continuous top surface of the anti-ligature device; or the tub is a cylindrical tub, the top sealing portion of the tub sealing element is a cylindrical lid, the insertion portion of the tub sealing element is an insertion cylinder, the insertion cylinder coupled to the cylindrical lid and has and insertion cylinder circumference, the lid circumference being greater than the insertion cylinder circumference such that a lip portion of the cylindrical lid is formed as defined by a portion of the cylindrical lid that extends outside the insertion cylinder circumference.

In yet other particular preferred variations of the device, the device further provides the tub sealing element is rotatable with respect to the tub, the insertion portion of the tub sealing element has at least one engagement pin attached to the insertion portion, the tub has at least one engagement slot, the engagement pin sliding within the engagement slot between a first position associated with the closed position of the anti-ligature device and a second position associated with the open position of the anti-ligature device; or the tub sealing element has at least one lock, the lock has an engagement element that secures the tub sealing element to the tub at a locking element within the tub when the anti-ligature device is in the closed position; or the at least one lock includes at least one locking pin coupled to the insertion portion, the tub includes at least one key hole on the inner surface of the tub, the tub sealing element includes a keyway coupled to the locking pin, the keyway disposed on the top surface of the tub sealing element, the keyway used to engage the at least one locking pin in the key hole in the tub when the tub sealing element is in the fully inserted position and the keyway is activated; or the at least one lock includes at least one locking pin coupled to the insertion portion and a keyway coupled to the locking pin, the keyway disposed on the top surface of the tub sealing element; or the compressible element is a spring, the bottom portion of the tub has a groove on the interior surface at a bottom portion of the tub, the first end of the spring being coupled to the bottom portion of the tub by being seated within the groove within the tub, the insertion portion of the tub sealing element has a lower surface, the lower surface has a groove, the spring coupled to the lower surface of the insertion portion by being seated within the groove on the lower surface of the insertion portion . . . ; or the tub securing element is a threaded rod, the bottom portion of the tub includes a threaded hole through which the threaded rod is coupled, the mounting location hole has is a double expansion-type anchor, the double expansion-type anchor is secured to the environment when the threaded rod is engaged with the double expansion-type anchor.

In a particularly preferred method according to the present invention a method of locking an anti-ligature device is provided, including the steps of pushing the tub sealing element at the top surface to release the tub sealing element from the first position; rotating the tub sealing element in relation to the tub; releasing the tub sealing element to allow the compressible element to force the tub sealing element and the device to attain the second position and expose the slot to the environment; securing a restraint using the slot; unsecuring the restraint from the slot; pushing the tub sealing element at the top surface; rotating the tub sealing element in relation to the tub to force a compression of the compressible element and cause the tub sealing element and the device to attain the first position; and locking the device in the first position by engaging the lock.

The objects and features of the present invention may be applied jointly or severally in any combination or sub-combination by those skilled in the art.

BRIEF DESCRIPTION OF THE SEVERAL VIEWS OF THE DRAWING(S)

Detailed embodiments of the present invention(s) are disclosed herein; however, it is to be understood that the disclosed embodiments are merely exemplary of the invention(s), which may be embodied in various forms. Therefore, specific structural and functional details disclosed herein are not to be interpreted as limiting, but merely as a basis for the claims and as a representative basis for teaching one skilled in the art to variously employ the present invention(s) in virtually any appropriately detailed structure. Further, the terms and phrases used herein are not intended to be limiting, but rather to provide an understandable description of the invention(s).

The accompanying drawings, which are incorporated in and constitute part of this specification, illustrate embodiments and/or aspects of the invention and/or disclosure, and together with the written description, these drawings serve to explain the principles of the invention. Wherever possible, the same reference numbers are used throughout the drawings to refer to the same or like elements of an embodiment. The embodiments illustrated herein are presently preferred, it being understood, however, that the invention is not limited to the precise arrangements and instrumentalities shown, in which:

FIGS. 1A-1D show top front and side views respectively of the apparatus according to one embodiment of the present invention;

FIGS. 2A-2B shows the top and side views respectively of a bed in an environment in which the present invention may be used;

FIGS. 4A-4C show the side, oblique and top views respectively of the tub according to one embodiment of the present invention;

FIG. 5 shows a top view of parts of the tub sealing element according to one embodiment of the present invention;

FIGS. 6A-6D show the bottom, side, front and oblique views respectively of the locking pins according to one embodiment of the present invention;

FIGS. 7A-7C show the top, oblique and side view of the securing cap according to one embodiment of the present invention;

FIGS. 8A-8D, including FIGS. 8C' and 8D', show the side, top, bottom and multiple oblique views respectively of the keyway lock element according to one embodiment of the present invention;

FIGS. 9A-9D show the top, oblique, sectional and side views of the lock cup according to one embodiment of the present invention;

FIGS. 10A-10D illustrate a series of partial assembly drawings of the tub sealing element in various stages of assembly according to one embodiment of the present invention.

Figure 12:
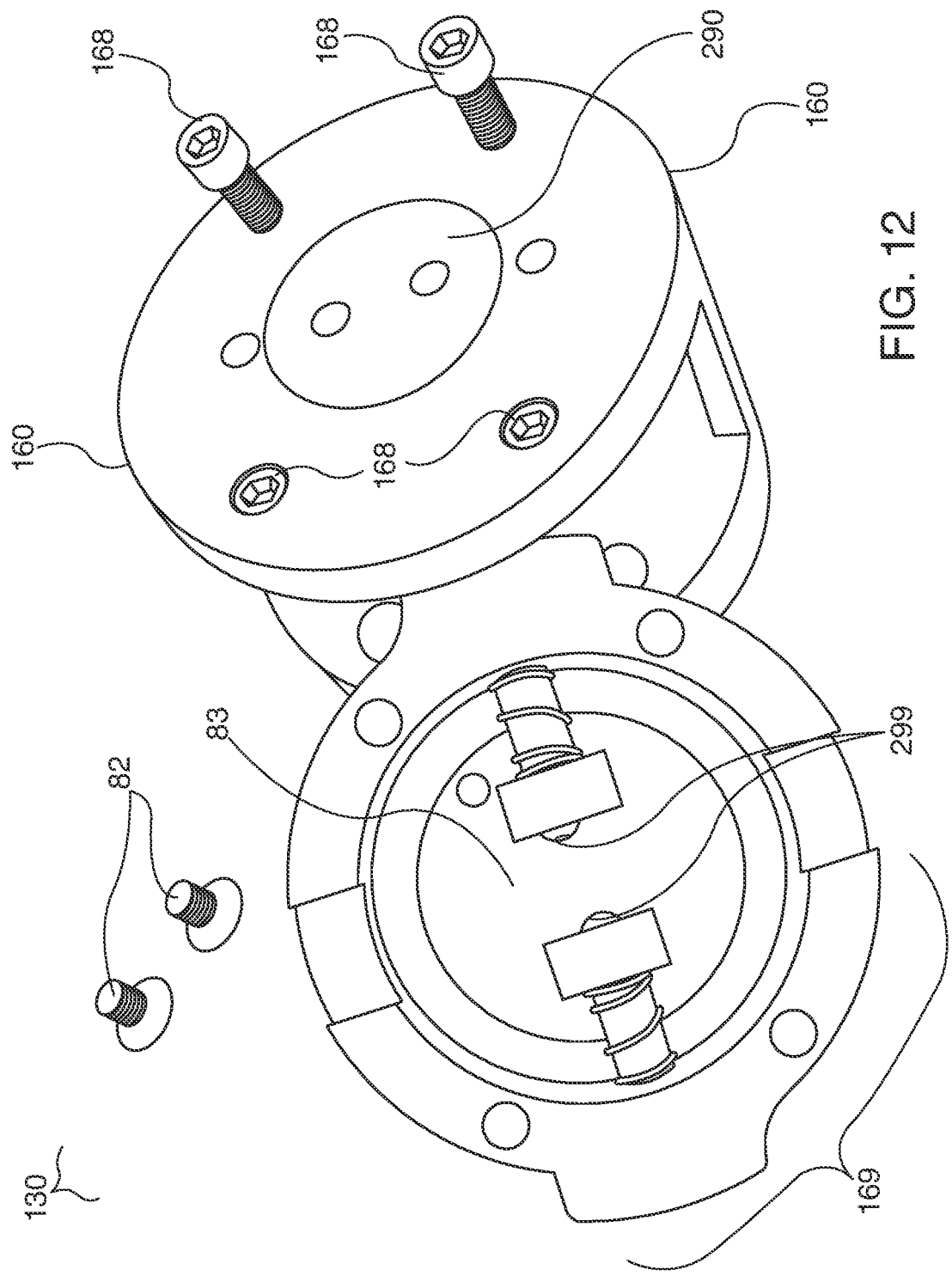
Figure 13A:
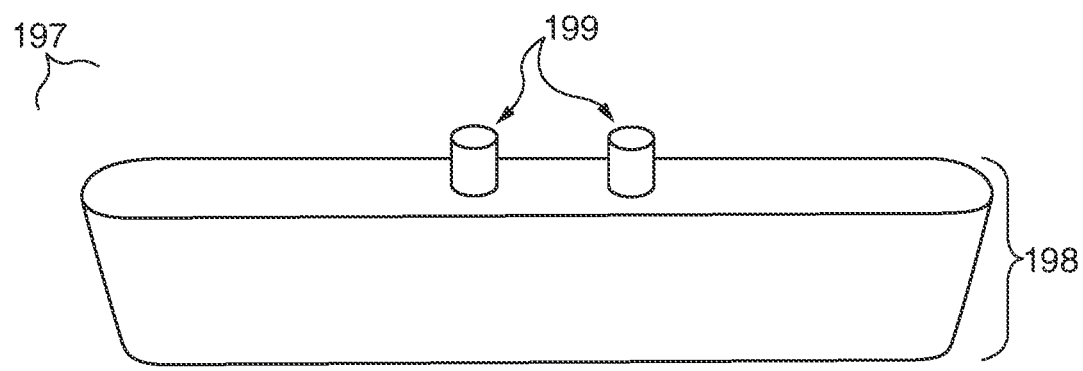
Figure 13B:
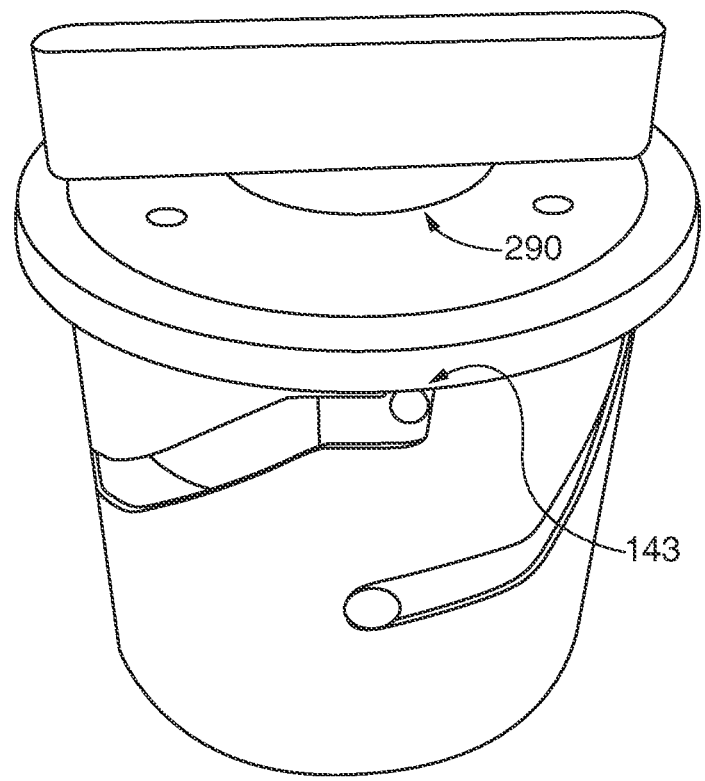

FIGS. 11A-11D show the top, bottom sectional and side views of the interior restraint element according to one embodiment of the present invention;

FIG. 12 illustrates a partial assembly drawing of the tub sealing element in one stage of assembly according to one embodiment of the present invention; and FIGS. 13A-13B illustrate the spanner key according to one embodiment of the present invention.

DETAILED DESCRIPTION OF THE INVENTION

To facilitate a clear understanding of the present invention, illustrative examples are provided herein which describe certain aspects of the invention. However, it is to be appreciated that these illustrations are not meant to limit the scope of the invention and are provided herein to illustrate certain concepts associated with the invention.

The entire description below is provided in the particular context of a patient restraint system for use in a hospital setting, and in particular a strap restraint system used with mentally handicapped patients in a clinical and protective hospital room. However, the invention of the present application is generally applicable to any other restraint systems in which any object requires secure restraint in one situation and an "invisible locked and secure presence" in a second situation.

FIGS. 1A-1D show the anti-ligature device of the present invention in four different views (respectively): FIG. 1A a top view, FIG. 1B a front view (fully-inserted, closed or first position), FIG. 1C a side view (not fully-inserted, exposed or second position), and FIG. 1D another front view (not fully-inserted, exposed or second position). As shown, anti-ligature device 1 includes a tub 10, shown as a cylindrical enclosure. Tub 10 contains most of the other device components and is coupled to the other elements of the present invention. Tub 10 has outer surface 9, extending a depth to 12 and having an external tub diameter 14. Tub 10 includes a lip 11 at the top of the top. Lip 11 extends radially beyond tub outer surface 9 to a lip diameter 13 that is greater than the tub diameter 14. Tub 10 includes an inner volume 20 that is defined by the tub inner surface 19 having an inner tub diameter 15. Slot 18 is provided on tub 10 and extends through the entire tub, from inner to outer surface, so that a channel is formed within tub 10. The channel provides for access between the exterior of tub 10 and the inner volume 20. Preferably, slot 18 is geometrically configured in the shape of an "S," a "Z" or a "C" as viewed from the tub side such that there are three portions of the slot—a first and a second (or top and bottom respectively) generally horizontal slot portions 18' and one, generally vertical, slot portion 18" conjoining the two horizontal slot portions.

Tub 10 sits securely within a hole or mounting location 3. FIG. 2. Tub securing element 25 is coupled to a tub bottom portion 16 of tub 10. Tub securing element 25 is secured to the environment within the mounting location. In one preferred embodiment, tub securing element is a threaded screw or bolt that is secured to the bottom portion 16 of tub 10. In this arrangement, the bottom portion 16 of tub 10 may have a threaded nut encased as part of the tub structure for threadable engagement with the tub securing element 25. The environment (hole) may itself have a hole or a depression in which some type of anchor 7 may be disposed. A double expansion anchor maybe be embedded when the mounting hole is concrete or other hard substance. A straight bolt and washer may also be used on wood surfaces and other solid objects that have access to the back side of the object. When the threaded screw or bolt is placed in the hole and engaged with the double expansion type anchor, an outer portion of the anchor expands to fill the embedded location in which it sits and the threaded bolt then pulls the inner portion of the double expansion anchor into a secure adherence position such that tub 10 then sits securely anchored in mounting location 3.

Mounting location 3 can be a wall, a floor or other solid object of some depth and/or securing capability such that tub 10 and tub securing element 25 may be used to anchor the tub in a somewhat permanent fashion within that solid element. Flat mounting surface 5 is necessarily a part of the solid object and mounting location 3. The top surface of tub lip 11 is necessarily seated below the flat mounting surface 5, or at a minimum is flush with flat mounting surface 5 when the tub 10 is fully inserted into mounting location 3 and secured with tub securing element 25. This is important so that no portion of the tub 10 is accessible, bendable, pryable or otherwise capable of deformation or removal by the patient in the hospital room. In this regard, and in an ideal arrangement, the top surface of tub lip 11 is not only flush with flat mounting surface 5, but lip diameter 13 of lip 11 is dimensioned to precisely fit within any indentation made within the mounting location to accommodate tub 10 and lip 11 so that a continuous and smooth surface is achieved when the tub 10 is fully inserted into mounting location 3 and secured with tub securing element 25.

Compressible element 26 is disposed within inner volume 20 and coupled to bottom portion 16 of tub 10 at a first end 27. Compressible element 26 is coupled at a second end 28 to tub sealing element 30. Tub sealing element 30 is dimensioned to fit within inner volume 20 of tub 10. Compressible element 26 is compressed upon the insertion of tub sealing element 30 within inner volume 20 such that an upward force is applied to the tub sealing element 30 by the compressible element when the device is in the closed position and tub securing element 30 in its fully inserted position. In FIG. 1B, the device is shown in the first position, with the tub sealing element 30 in a fully inserted (closed position). In FIG. 1D, the device is shown in the second position, with the tub sealing element not fully-inserted (open position) and at least partially exposed to the environment.

Tub sealing element 30 is generally comprised of two portions coupled together: an insertion portion 40 and top sealing portion 32. Insertion portion 40 is coupled to the second end 28 of the compression element 26 at its bottom and to the top sealing portion 32 at a lower surface 33 thereof. As shown in FIGS. 1A-1D, insertion portion 40 also has at least one dimension that has an outer diameter 34 that is slightly smaller than inner tub diameter 15. In the embodiment illustrated in FIGS. 1A-1D, insertion portion 40 is cylindrical as viewed from the top (FIG. 1A) and has a generally rectangular solid form 42 as viewed from the front (FIGS. 1B, 1D). Insertion portion 40 has curved outer edge surfaces and a rectangular hole or slot 46 within the rectangular solid 42. In FIG. 1C, the side view of the rectangular solid comprising the insertion portion 40 is shown. In FIG. 1B, a front view of the rectangular insertion portion is shown as fully inserted into inner volume 20 of tub 10.

As shown in FIG. 1A, top sealing portion 32 is circular with a shallow depth 33 so as to comprise a shallow cylinder. Top sealing portion has an outer diameter that fits comfortably but snugly within inner lip diameter/outer tub diameter 14 when the tub sealing element is fully inserted into tub 10. Top sealing portion 32 includes locking pins 93 on the outer periphery of the cylinder. Locking pins 93 may be solid non-compressible protrusions that extrude from the outer periphery of the top sealing portion 32. One or more keyways 90 may be coupled to said locking pins may be included within or on the top of top sealing portion 32. Keyways 90 are rotatable such that rotation in one direction retracts the locking pins within the top sealing portion and rotation in the other direction extends them out beyond the periphery of the outer diameter 34 of the top sealing portion 32. Locking holes 94 are provided as indents on the inner tub surface 19 and are disposed at certain registered locations at the top portion of the tub 10. When the device is in the final, first closed position, the locking pins 93 are aligned with the locking holes 94 and the keyway may be turned to extend the locking pins into the locking holes and secure the entire tub securing element in a locked relationship with tub 10.

Engagement pins 43 are included as part of the structure of the insertion portion 40 and are slidably inserted into holes in the profile edges of insertion portion 40, preferably at a bottom portion thereof and slightly above the point at which the insertion portion is coupled to the second end 28 of compressible element 26. Springs may be used behind the engagement pins 43 so that the pins are naturally pushed out and away from the body of the insertion portion 40. When the top sealing portion 32 is fully inserted into tub 10, and in the fully assembled device arrangement, the engagement pins are aligned with the first horizontal slot portion upon insertion of the tub sealing element. As the tub insertion element is first inserted into tub 10, the pins 43 "pop out" when they engage with the top-most, first horizontal slot portion 18'. Once assembled, and both engagement pins 43 (one on each of the two sides of insertion portion 40) "pop out" and engage with slots 18, the anti-ligature device is fully assembled. Once fully assembled, pins 43 remain engaged in slots 18 for the duration of the operational life of the anti-ligature device, traversing the slots from one horizontal portion, through the vertical portion and then through the other horizontal portion. Engagement pins 43 may also be "T-shaped" as viewed from the side of the pin (pin profile). In this arrangement, they are of sufficient diameter to be positioned in the slot 18 and securably screwed into insertion portion 40 of the tub securing element 25 as permanently affixed within tub 10 so as to create the final assembly.

The anti-ligature is operable between the second position shown in FIG. 1D to the first position shown in FIG. 1B in the following manner. Transitioning the anti-ligature device is accomplished by pushing the tub sealing portion 32 down at the top surface 35, against the upward force exerted by the compression element 26. Simultaneous with the exertion of downward force, tub sealing element is rotated counter-clockwise (as viewed from the top) in relation to tub 10 so that engagement pins 43 travel along the upper horizontal slot portion 18' over to the joinder location of slot portion 18 with vertical slot portion 18". Continuing with the application of downward force, tub sealing element 30 is pushed into tub 10 and engagement pins 43 travel down along vertical slot portion 18" of slot 18 and to the joinder of vertical slot portion 18" with lower horizontal slot portion 18'. To complete the transition from the second device position to the first device position, the tub sealing element is rotated by the force placed on top surface 35 again simultaneously with the exertion of downward force, in a counter-clockwise (as viewed from the top) in relation to tub 10 so that engagement pins 43 travel along the lower horizontal slot portion 18' over to the end of that horizontal slot portion.

It should be appreciated that in both the first (closed) and second (exposed) device positions the compression element applies an upward force on tub sealing element 30 at all times. When fully compressed, and the device is fully disposed in closed device position, the engagement pins 43 are forced against a top edge of the lower horizontal slot portion 18'. In this position, the compression element provides the greatest force on tub sealing element 30. When fully exposed, and the device is fully disposed in the second device position, the engagement pins 43 are forced against a top edge of the upper horizontal slot portion 18'. In this position, the compression element provides the least force on tub sealing element 30.

It should also be appreciated that the geometry of slot 18 can be any one of several shapes such that the above functions are accommodated. Thus an "S-shaped" or a "C-shaped slot" may be employed. In the case of a "C-shaped" slot the rotation direction of the tub sealing element would need to be reversed when transitioning between the two device positions. Most desirably, a "Z-shaped" slot is preferred so that the simultaneous application of force and rotation on the tub sealing element is more easily performed. Finally, registration notches 21 (FIG. 4A) may be included at terminal and interstitial points along the travel path of engagement pins 43 within slot 18 such that the transition may be partially completed and "stored" mid-way, or may otherwise be securely terminated at the ends of the slots. In fact, in experimental use, the registration notches 21 at the ends of slot 18 proved to be the most secure and safe method of securing the tub sealing element 30 in final resting positions and preventing inadvertent rotation of the tub sealing element when in those positions.

Is should be further be appreciated that different configurations and constructions of the tub and internal components may be achieved in accord with the teachings of the present invention. First, different tub geometries may be used.

Square tubs, triangular tubs, truncated frustrum and other shapes of tubs are envisioned. Top portions of the top sealing portion may be maintained as round, and rotatably engageable within a round top hole in the top of an otherwise non-cylindrical tub. Different internal components and pinhole or pin-slot arrangements may be used to accommodate variations to the basic geometric structures herein. The basic teachings provided herein are applicable, nonetheless. Further, the construction of the components may vary or be mixed and matched. The requisite parts may be cast metal, mild steel, with powder coating, stainless steel, high strength aluminum, molded plastic, 3D-printed material or combinations of any of the same, such that the objectives of the present invention are achieved. Also, different tub securing elements (hooks, clasps, hasps, rope, bolted platforms etc.) as well as different compression elements (pistons, hydraulics, deformable solids etc.) may be substituted so that the objectives of the invention herein are accomplished.

FIG. 2 shows an exemplary environment in which the anti-ligature device of the present invention is used. Patient bed 2 is provided disposed on a floor of the environment. The anti-ligature devices are embedded in the floor or mounting locations 3. In the hospital setting, the floor may be concrete and mounting holes 3 may be provided in the floor to a mounting depth 4. The flat mounting surface 5 is the floor surface. Tub sealing element 30 extends above the floor surface in the opened position so that the restraint element slot 46 is exposed to the environment. Straps may then be threaded through the one or more exposed restraint element slots and across the bed 2 so as to restrain the patient thereto.

Figure 3:
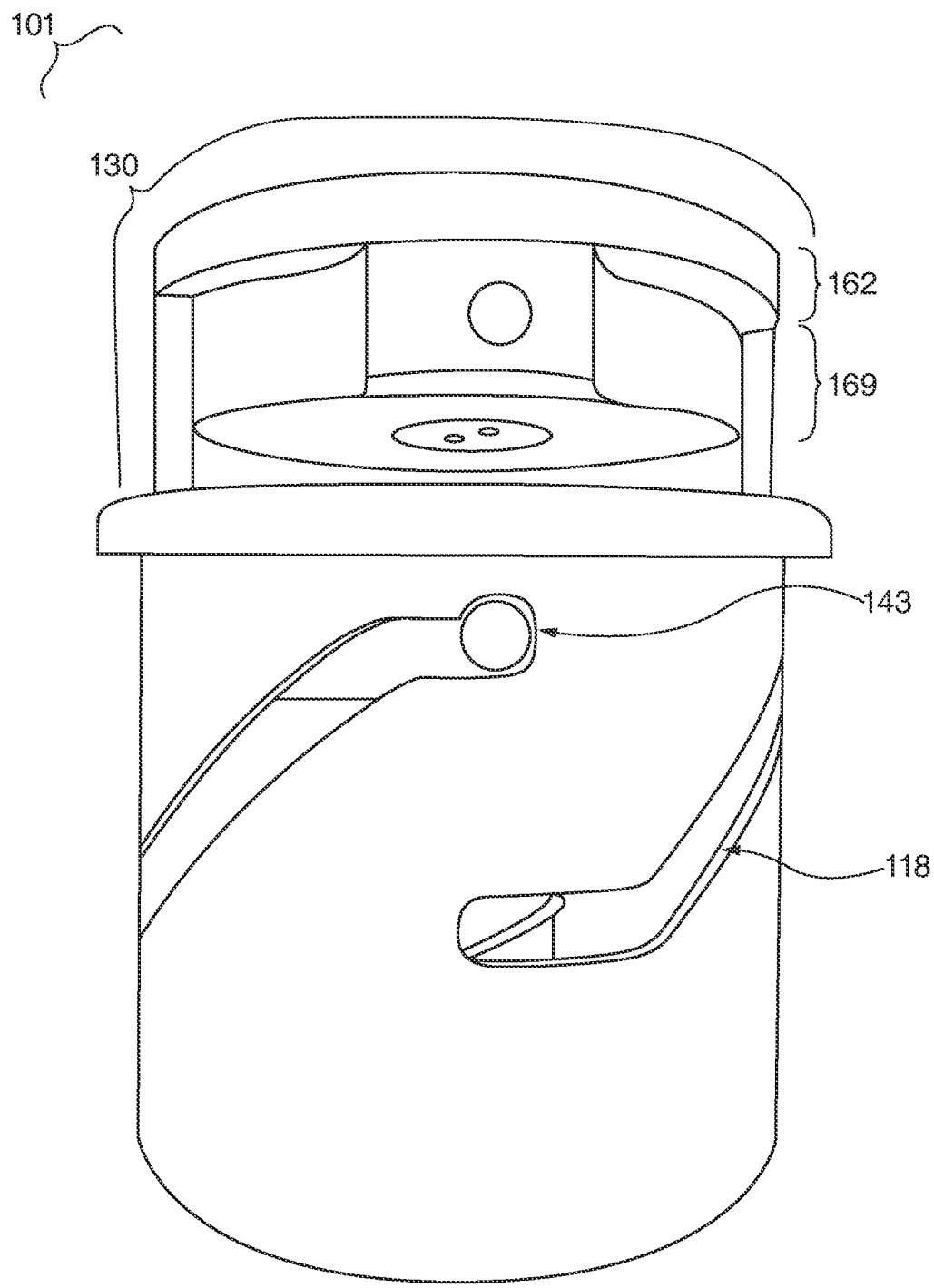
FIG. 3 shows a full front view of the device according to one prototype embodiment of the invention.

A particularly preferred prototype of the anti-ligature device of the present invention has been invented and is described herein in detail with respect to the following figures. FIG. 3 shows prototype anti-ligature device 101. In this embodiment, a mild steel construction having a powered coating is used for construction of the main structural pieces. When used in a floor and corrosion is of concern, a stainless steel construction may be desirable. In other applications high strength aluminum may be used as a fabrication material. FIG. 3 provides an oblique view of the device as fully assembled and displayed in the second (exposed, not fully-inserted) position.

FIGS. 4A-4C show, respectively, a front view, an oblique view, and a top view of the tub of the anti-ligature device according to one particularly preferred prototype embodiment of the present invention. Exemplary dimensions are included on the figures only as a reference as to the size of this embodiment (and are incorporated by reference to the FIGs. in the written portion of this specification in their entirety). FIG. 4A shows the tub 110 as it is inserted into mounting location (a hole in the floor) 103. The mounting location 103 is formed so that an annular recessed portion 106 of the mounting location is formed at mounting surface 105 and at the outside the diameter of the main mounting hole. Lip 111 of tub 110 then sits in that recessed annular region. In this position, the top of the top surface of the lip is flush with the mounting surface 105. Tub securing element 125 is shown as a threaded bolt that is secured to a bottom portion 116 of tub 110. Tub 110 has a threaded hole 122 in the center of the bottom thereof. As mentioned above, the mounting location 103 includes a recessed additional hole at the center bottom in which a double expansion anchor 107 maybe embedded. The dimensions of the tub 110 and the mounting location are tightly controlled and coordinated with respect to one another, and in particular the tub exterior diameter 114 and the diameter of the mounting location are matched so that a tight insertion fit is achieved when the tub 110 is fully inserted into the mounting location. In practical application, the tub may be inserted into mounting location without the tub sealing element 130 and the tub securing element 125 may be screwed "through" the threaded hole provided at the bottom of the bottom tub portion 116 of tub 110 and straight on through to a double expansion anchor 107 beneath the tub 110. Full insertion and tightening will then simultaneously expand and lock the double expansion anchor 107 to the mounting location 103 and secure tub 110 in place in that mounting location 103.

As shown in FIGS. 4A and 4B, four "zig-zag" or "Z-shaped" slots 118 are provided at the for ordinal positions of the tub, i.e. disposed evenly at 90 degrees from one another around the tub. Each slot 118 has two substantially horizontal portions 118' and one substantially vertical portion 118". As previously described, the engagement pins 143 attached to the tub sealing element engage in these slots to provide for slidable movement along the slots when the tub sealing element is transitioned from the first to the second positions and back again.

FIG. 5 shows locking pins 293, with springs 95 attached thereto and securing cap 83. Locking pins 293 are shown in greater detail in FIGS. 6A-6C. Securing cap 83 is shown in greater detail in FIGS. 7A-7C.

FIGS. 6A-6D show, respectively, a bottom view, a side view, a front view and an oblique view of the locking pins 293 according to one particularly preferred prototype embodiment of the present invention. Exemplary dimensions are included on the figures only as a reference as to the size of this embodiment (and are incorporated by reference to the FIGs. in the written portion of this specification in their entirety). Locking pins 293 include head end pin portion 213, pin stem 215 and ridge 217 on pin stem 215.

FIGS. 7A-7C show, respectively, a bottom view, an oblique view and a side view the securing cap according to one particularly preferred prototype embodiment of the present invention. Exemplary dimensions are included on the figures only as a reference as to the size of this embodiment (and are incorporated by reference to the FIGs. in the written portion of this specification in their entirety). Securing cap 83 includes recessed annular region 86, dowel turn stop 84, and through holes 85.

FIGS. 8A-8D, including FIGS. 8C' and 8D', show, respectively, a side view, a top view a bottom view and three different oblique views of the keyway lock element 290 according to one particularly preferred prototype embodiment of the present invention. Exemplary dimensions are included on the figures only as a reference as to the size of this embodiment (and are incorporated by reference to the FIGs. in the written portion of this specification in their entirety). Keyway lock element 290 includes a head portion 292 having a flanged or chamfered edge 291. The head portion 292 is coupled to key stem 294 and includes key holes 296. The key stem 294 has an undulating edge profile 295 such that its edge swoops in an out with respect to a central axis 297 of said keyway lock element 290.

FIGS. 9A-9D show, respectively, a top view, an oblique view, a side sectional view and a side view of the lock cup 172 according to one particularly preferred prototype embodiment of the present invention. Exemplary dimensions are included on the figures only as a reference as to the size of this embodiment (and are incorporated by reference to the FIGs. in the written portion of this specification in their entirety). Lock cup 172 is generally annular in shape. The annular lock cup 172 includes mounting holes 174 drilled vertically therethrough. Lock cup 172 has an inner annular ledge 175 disposed at the bottom of the annular lock cup 172. The inner annular ledge 175 includes a locking pin seat 176. Locking pin holes 178 are drilled laterally through the side of lock cup 172 from the locking pin seat 176 to the lateral exterior wall of the lock cup 172. Securing pin holes 179 are included transverse to the locking pin holes 178 within the annular ring. Securing pin holes are 179 are preferably threaded and are drilled through to meet the locking pin holes 178 at a midpoint thereto. A threaded securing pin 399 is provided to be threadedly engaged in securing pin holes 179 so as to be able to contact locking pin holes 178. The securing pin is inserted into securing pin hole 179 so as to prevent locking pins 293 from retracting too far back into lock cap 172 by "catching" the pins at ridge 217.

Figure 10A:
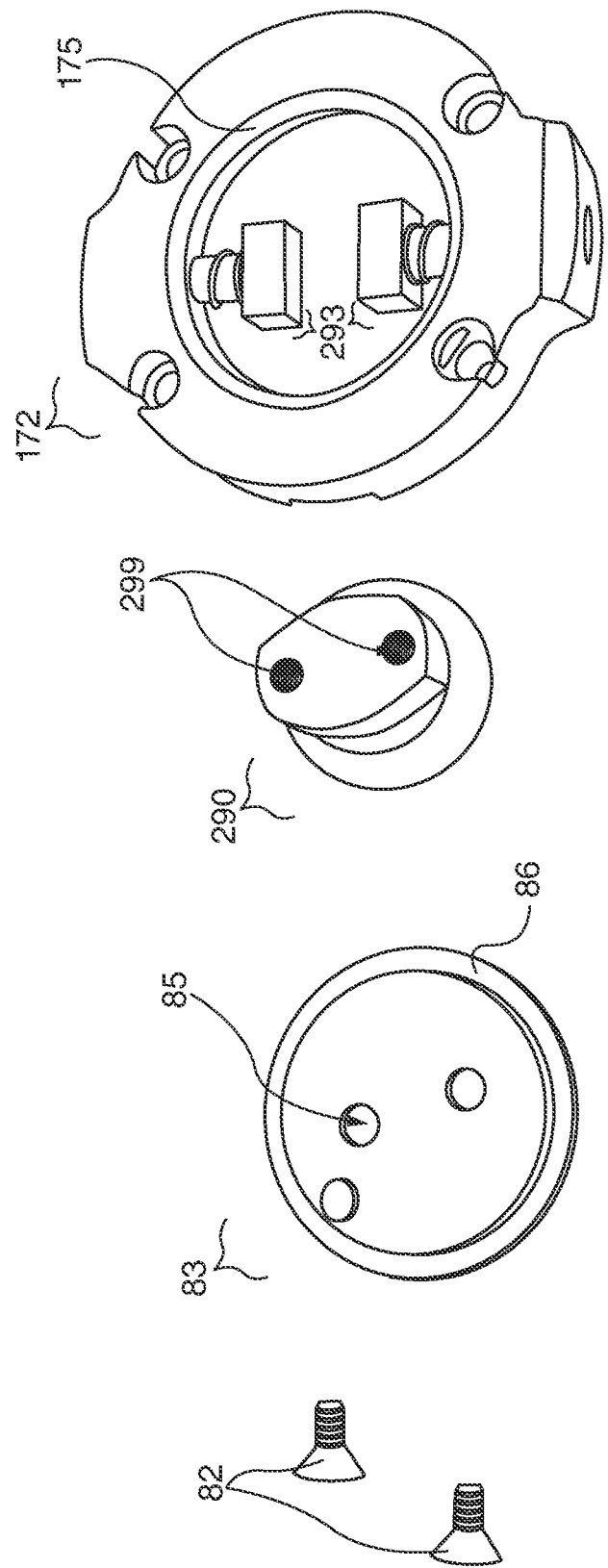

FIGS. 10A-10D illustrate a series of assembly drawings of the parts of the tub sealing element 130 in various stages of assembly according to one particularly preferred prototype embodiment of the present invention. In FIG. 10A, a bottom view of each of the unassembled assembly components is shown. Mounting screws 82 are positioned for insertion through mounting holes 85 in securing cap 83. Securing cap 83 is positioned for covering the bottom of lock cup 172 such that recessed annular region 86 rests against the downward facing inner annular ledge 175 of locking cap 172. The diameter of securing cup 83 matches the diameter of the inner edge of central annular area of locking cup 172. Keyway lock element 290 has keyway mounting holes 299 on the bottom of key stem 294 thereof for mateable coupling with mounting screws 82 when keyway lock element—turned upside-upside down—is inserted into the top of the annular ring (i.e. from the backside of lock cap 172 as shown in FIG. 10A).

In FIG. 10B, a top view is shown of the upper restraint assembly 169 is shown including the following components: locking pins 293 and securing cap 83. Locking pins 293 have the springs 95 inserted over the pin stem 215 and are inserted into the locking pin holes 178.

Figure 10C:
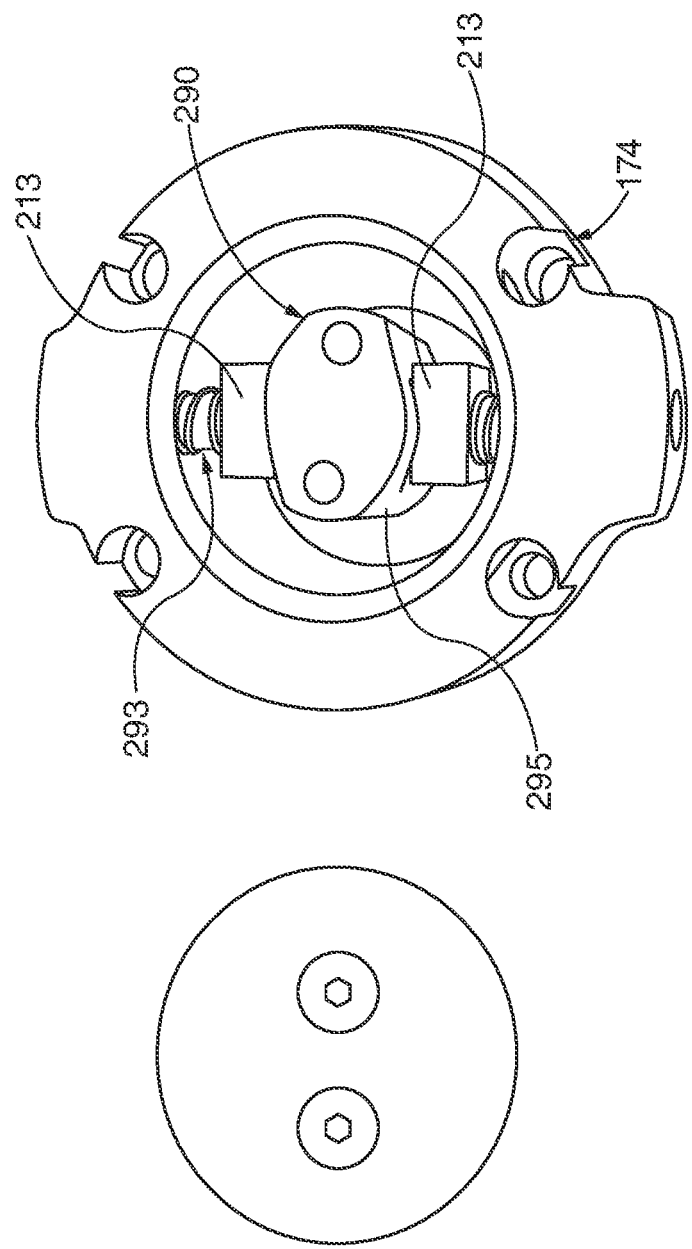

In FIG. 10C, a bottom view is shown of the partially assembled tub sealing element 130 including the following components: locking pins 293 and keyway lock element 290. Locking pins 293 have the springs 95 inserted over the pin stem 215 and are inserted into the locking pin holes 178. Locking pin head ends 213 rest on the undulating edges of 295 of fully inserted keyway locking element 290. It should be appreciated that the assembly of FIG. 10C omits the interposing interior restraint element onto the bottom of which is affixed the lock cup 172 and the top of which accommodates the keyway lock element 290. It should also be noted that mounting holes 174 are accessed for assembly from the underside of the tub sealing element and through access holes in the bottom of the interior restraint element.

In FIG. 10D, a top view is shown of the partially assembled tub sealing element 130 as provided in FIG. 10C but further including the securing cup 83 assembled thereto at the bottom surface. Again, the following components are included: locking pins 293 and keyway lock element 290. Locking pins 293 have the springs 95 inserted over the pin stem 215 and are inserted into the locking pin holes 178. Locking pin head ends rest on the undulating edges of 295 of fully inserted keyway lock element 290. It should be appreciated that in one rotational position of the keyway lock element the undulating edges of key stem 294 exert force on the pin heads end 213 causing the locking pins 293 to be pushed through the locking holes 294 and out the sides of the annular region of the lock cup 172. In this position, the springs 95 exert force on the key stem 213 and cause push back force into the annular ring. Dowel turn stop 84 provides for a stopping mechanism in the rotation of keyway lock element 290 so that the appropriate rotation of the keyway is provided to effect sufficient pin stem insertion without allowing the keyway lock element 290 from progressing past a maximal point of pin stem extension. Again, it should be appreciated that the assembly of FIG. 10D omits the interposing interior restraint element onto the bottom of which is affixed the lock cup 172 and the top of which accommodates the keyway lock element 290. This has been omitted to show clearly the workings of the keyway lock element rotation and engagement of the locking pins.

FIGS. 11A-11D show, respectively, a top view, a bottom view, and a section view and a front view the interior restraint element 160 according to one particularly preferred prototype embodiment of the present invention. Exemplary dimensions are included on the figures only as a reference as to the size of this embodiment (and are incorporated by reference to the FIGs. in the written portion of this specification in their entirety). Interior restraint element 160 is generally cylindrical as shown in the top view of FIG. 11A. Top restraint disk 162 has a hole in the middle of the top 161 with a chamfered edge 163 on the hole edge. Restraint sidewalls 164 are coupled to the top restraint disk at opposite sides of the top restraint disk 162. Only one restraint side wall is shown in the side view of FIG. 11C with the second being disposed directly behind the one being showing in that FIG. Bottom restraint disk 166 is coaxial with top restraint disk 162 and is of the same diameter and size. Along with the upper restraint assembly 169 (described below) restraint sidewalls 164 are coupled to the bottom restraint disk at opposite sides of the bottom restraint disk. Restraint disks 162 and 166, coupled by restraint sidewalls provide for an open form cylindrical element (in combination with all other attached elements—one tub sealing element 130) for insertion into tub 110.

FIG. 11D shows a full front profile of the interior restraint element 160 including the restraint element slot 146. In a fully assembled tub sealing element, the lock cup 172, securing cap 183 and locking pins 93 (together upper restraint assembly 169) are all presented into the middle of interior restraint element 160 by insertion through slot 146 as shown in FIG. 12. After insertion of the lock cup and associated parts, the components are assembled as follows.

Four through holes 167 are provided on the bottom of bottom restraint disk 166. These through holes are dimensionally arranged the same as the four mounting holes 174 on the bottom of lock cup 172. The through holes 167 are provided to allow screwdriver/allen wrench access through the bottom restraint disk 166 and the restraint element slot 146 to the long mounting screws 168 shown in FIG. 12. Using long mounting screws 168, the upper restraint assembly 169 may be inserted into place and secured to the underside of the top restraint disk 162 of interior restraint element 160. Is should be appreciated that for the locking pins 93 to work, the upper restraint assembly ideally orients the locking pins pointing out the side of the interior restraint perpendicular to the restraint element slot 146, i.e. pointing straight out the sides as shown in FIG. 11D. Finally, once the long mounting screws 168 have been fully inserted there is a small space in the screw holes 268 in the top restraint disk 162. These small spaces may be sealed over with putty, glue or other composite material to prevent top-side access to the screw ends at the top surface of the top restraint disk, which sits exposed at the flush surface of the flat mounting surface 5.

Two through holes 267 are also provided on the bottom of bottom restraint disk 166. These through holes are arranged so as to register with the two mounting holes 85 on securing cap 83. The through holes 267 are provided to allow screwdriver/allen wrench access through the bottom restraint disk 166 and the restraint element slot 146 to the mounting screws 82 shown in FIG. 10A. Using mounting screws 82, the securing cap 83 may be inserted into place within the upper restraint assembly 169, simultaneously with the insertion of the keyway locking element 290 into chamfered hole 161 and secured to the keyway locking element 290 at keyway mounting holes 297. This assembly difficulty should be appreciated in that keyway locking element 290 is inserted into the top restraint disk 162, while simultaneously inserting the upper restraint assembly 169 into the interior restraint element 160 and aligning the undulating edges 295 of key stem 294 such that proper registration of all parts is made upon assembly.

Also shown in the sectional view FIG. 11C are two half sections of engagement pin receptacles 243. Engagement pin receptacles are configured for receiving engagement pins 143 as shown in FIG. 3. Again, these engagement pins are permanently attached to the tub sealing element 130, and once the tub sealing element 130 is inserted into the tub 110 they are permanently disposed within slots 118 on tub 110 for slidable operation of the device as it transitions between the exposed and closed positions.

FIG. 12 shows a partial assembly arrangement of the sealing element 130 the interior restraint element 160 having keyway locking element 290 inserted into chamfered hole 161 at the top surface thereof. Upper restraint assembly 169 is partially inserted into the restraint element slot 146 and long mounting screws 168 are positioned for securing the upper restraint assembly 169 to the interior restraint element 160 at the underside of top restraint disk 162. Next, mounting screws 82 are positioned for securing the securing cap 83 to the keyway locking element 290 at keyway mounting holes 299 from the bottom as viewed in FIG. 12. All mountings take place through access holes in the bottom restraint disk as previously described.

FIG. 13A show the spanner head key 197 used to rotate the keyway lock element 290 which throws the locking pins 293, via the operation of the undulating edge on 295 on key stem 294 so as to lock and unlock the tub sealing element 130 to the tub 110. In one particularly preferred embodiment, the locking pins 293 extrude out to the same tub holes/slot 118/registration notches 21 that are used for the engagement pins 143. Since locking only take place in the closed device position, the upper slot areas, particularly along the upper horizontal slot 118' are left vacant for use of the same by the locking pins 293. Spanner head key 197 includes handle portion 198 and key pins 199. Key pins 199 are inserted into key holes 293 as shown in FIG. 13B showing the fully-assembled anti-ligature device 101 in the first position. Key holes 293 are shown at the top of keyway locking element 290 and rotated to engage the locking pins. In operation, the compressible element 126 provides sufficient force on the tub sealing element 130 such that the keyway lock element cannot easily be rotated without the spanner head key 197.

The terms "a" or "an," as used herein, are defined as one or more than one. The term "another," as used herein, is defined as at least a second or more. The terms "including" and/or "having", as used herein, are defined as comprising (i.e., open transition). The term "coupled" or "operatively coupled," as used herein, is defined as connected, although not necessarily directly and mechanically.

While the invention has been disclosed in connection with the preferred embodiments shown and described in detail, various modifications and improvements thereon will become readily apparent to those skilled in the art. Accordingly, the spirit and scope of the present invention is not to be limited by the foregoing examples, but is to be understood in the broadest sense allowable by law.

Although various embodiments, which incorporate the teachings of the present invention have been shown and described in detail herein, those skilled in the art can readily devise many other varied embodiments that still incorporate these teachings.

The invention claimed is:

1. An anti-ligature device for use with restraints, the restraints used within an environment, the environment having a mounting location, said mounting location including a hole into which said anti-ligature device is mounted, said anti-ligature device comprising:

a tub, said tub being open at one end, said tub having an outer surface and an inner surface, said tub inner surface partially defining an inner cavity, said tub being dimensioned for insertion into said mounting hole such that said tub fits within said hole;

a tub securing element, said tub securing element secured to said inner surface of said tub and the mounting location;

a compressible element having a first end and a second end, said compressible element disposed within said inner cavity of said tub and coupled at said first end to said tub;

a tub sealing element, said tub sealing element having a restraint element for engaging the restraints, said tub sealing element coupled to said compressible element at said second end, said tub sealing element having an insertion portion and a top sealing portion, said top sealing portion of said tub sealing element coupled to said insertion portion, said insertion portion compressing said compressible element when said tub sealing element is inserted into said tub such that said tub sealing element is under force by action of said compressible element when inserted into said rub;

said tub sealing element being disposed apart from said tub by said compressible element in an open position of said anti-ligature device, said compressible element remaining within said inner cavity in said open position, said restraint element being exposed to the environment in said open position, said restraints capable of being operatively coupled to said restraint element in said open position, and said tub sealing element being inserted into said tub in a closed position of said anti-ligature device, said restraint element being disposed entirely with said tub in said closed position, and said top sealing portion of said tub sealing element sealing said open end of said tub in said closed position such that said restraint element is not exposed to the environment in said closed position and said restraints are not capable of being operatively coupled to said restraint element in said closed position.

2. The device of claim 1 wherein said environment is a room and said restraint is a restraining strap for restraining a person, said restraint element is a slot for receiving said restraining strap, and said mounting location within said environment is one of a floor, a wall, or a piece of furniture.

3. The device of claim 1 wherein said tub has a top surface at said open end, said top sealing portion of said tub sealing element has a top surface, said top surface of said tub and said top surface of said rub sealing element meeting to provide said seal between said tub sealing element sealing and said open end of said tub in said closed position.

4. The device of claim 1 wherein said tub has a top surface at said open end, said open end of said tub has a circumference profile, said top sealing portion of said tub sealing element has a top surface, said top surface of said top sealing portion has a circumference profile, said circumference profiles of said open end of said tub and said tub sealing element being identical, said circumference profile of said open end of said tub being slightly larger than said circumference profile of said tub sealing element, said top sealing portion of said tub sealing element fitting within said opening of said tub in said closed position such that said of said top surface of said tub is substantially coplanar with said top surface of said tub sealing element and providing said seal in said closed position.

5. The device of claim 4 wherein said tub is a cylindrical tub, said top sealing portion of said tub sealing element is a cylindrical lid, said insertion portion of said tub sealing element is an insertion cylinder, said insertion cylinder coupled to said cylindrical lid an having and insertion cylinder circumference, said lid circumference being greater than said insertion cylinder circumference such that a lip portion of said cylindrical lid is formed as defined by a portion of the cylindrical lid that extends outside the insertion cylinder circumference.

6. The device of claim 5 wherein said tub sealing element is rotatable with respect to said tub, said tub sealing element having an insertion portion, said insertion portion having at least one engagement pin attached to said insertion portion, said tub having at least one engagement slot, said engagement pin sliding within said engagement slot between a first position associated with said closed position of said anti-ligature device and a second position associated with said open position of said anti-ligature device.

7. The device of claim 1 wherein said tub sealing element has at least one lock, said lock having an engagement element that secures said tub sealing element to said tub at a locking element within said tub when said anti-ligature device is in said closed position.

8. The device of claim 7 wherein said at least one lock comprises at least one locking pin coupled to said insertion portion, said tub includes at least one key hole on said inner surface of said tub, said tub sealing element includes a keyway coupled to said locking pin, said keyway disposed on a top surface of said tub sealing element, said keyway used to engage said at least one locking pin in said key hole in said tub when said tub sealing element is in said fully inserted position and said keyway is activated.

9. The device of claim 8 wherein said at least one lock comprises at least one locking pin coupled to said insertion portion and a keyway coupled to said locking pin, said keyway disposed on said top surface of said tub sealing element.

10. The device of claim 1 wherein said compressible element is a spring, said bottom portion of said tub having a groove on an interior surface of said bottom portion of said tub, said first end of said spring is coupled to said bottom portion of said tub by being seated within said groove within said tub, said insertion portion of said tub sealing element having a lower surface, said lower surface having a groove, said spring coupled to said lower surface of said insertion portion by being seated within said groove on said lower surface of said insertion portion.

11. The device of claim 1 wherein said tub securing element is a threaded rod, said bottom portion of said tub includes a threaded hole through which said threaded rod is coupled, said mounting location hole having is a double expansion-type anchor, said double expansion-type anchor is secured to the environment when said threaded rod is engaged with said double expansion-type anchor.

\* \* \* \* \*